United States Patent [19]
Dam et al.

[11] 4,192,318
[45] Mar. 11, 1980

[54] METHOD AND APPARATUS FOR LOCATING THE QRS PORTION OF AN ELECTROCARDIOGRAPHIC SIGNAL

[75] Inventors: Naim G. Dam, Bayside; Monroe A. Landau, Kew Gardens, both of N.Y.

[73] Assignee: Bios Inc., Valhalla, N.Y.

[21] Appl. No.: 942,063

[22] Filed: Sep. 13, 1978

[51] Int. Cl.² ............................................. A61B 5/04
[52] U.S. Cl. ................................................ 128/708
[58] Field of Search ................. 128/2.06 R, 696, 703, 128/702, 708

[56] References Cited

U.S. PATENT DOCUMENTS

| 3,215,136 | 11/1965 | Holter et al. | 128/702 |
| 3,533,402 | 10/1970 | Siedband | 128/703 |
| 3,543,050 | 11/1970 | Paine | 128/696 |
| 3,590,811 | 7/1971 | Harris | 128/708 |
| 3,606,882 | 9/1971 | Abe et al. | 128/703 |
| 3,822,696 | 7/1974 | Ekstrom et al. | 128/703 |
| 3,878,832 | 4/1975 | Tickner et al. | 128/696 |

OTHER PUBLICATIONS

Dell'Osso, "IEEE Transactions on Biomedical Engineering", vol. BME-20, No. 1, Jan., 1973, pp. 43–50.
Brandon et al, "Computors and Biomedical Research 3", 1970, pp. 47–57.

*Primary Examiner*—William E. Kamm
*Attorney, Agent, or Firm*—McAulay, Fields, Fisher & Goldstein

[57] ABSTRACT

A method and improved apparatus for automatically locating the QRS portion of an electrocardiographic signal and for generating a corresponding synchronization pulse is disclosed. Properties associated with the QRS portion of an electrocardiographic signal are utilized in the implemenation of an adaptive peak detector capable of accurately operating with electrocardiographic signals varying in amplitude or polarity. The adaptive peak detector is also capable of discriminating against signal components lying outside certain predetermined limits.

28 Claims, 7 Drawing Figures

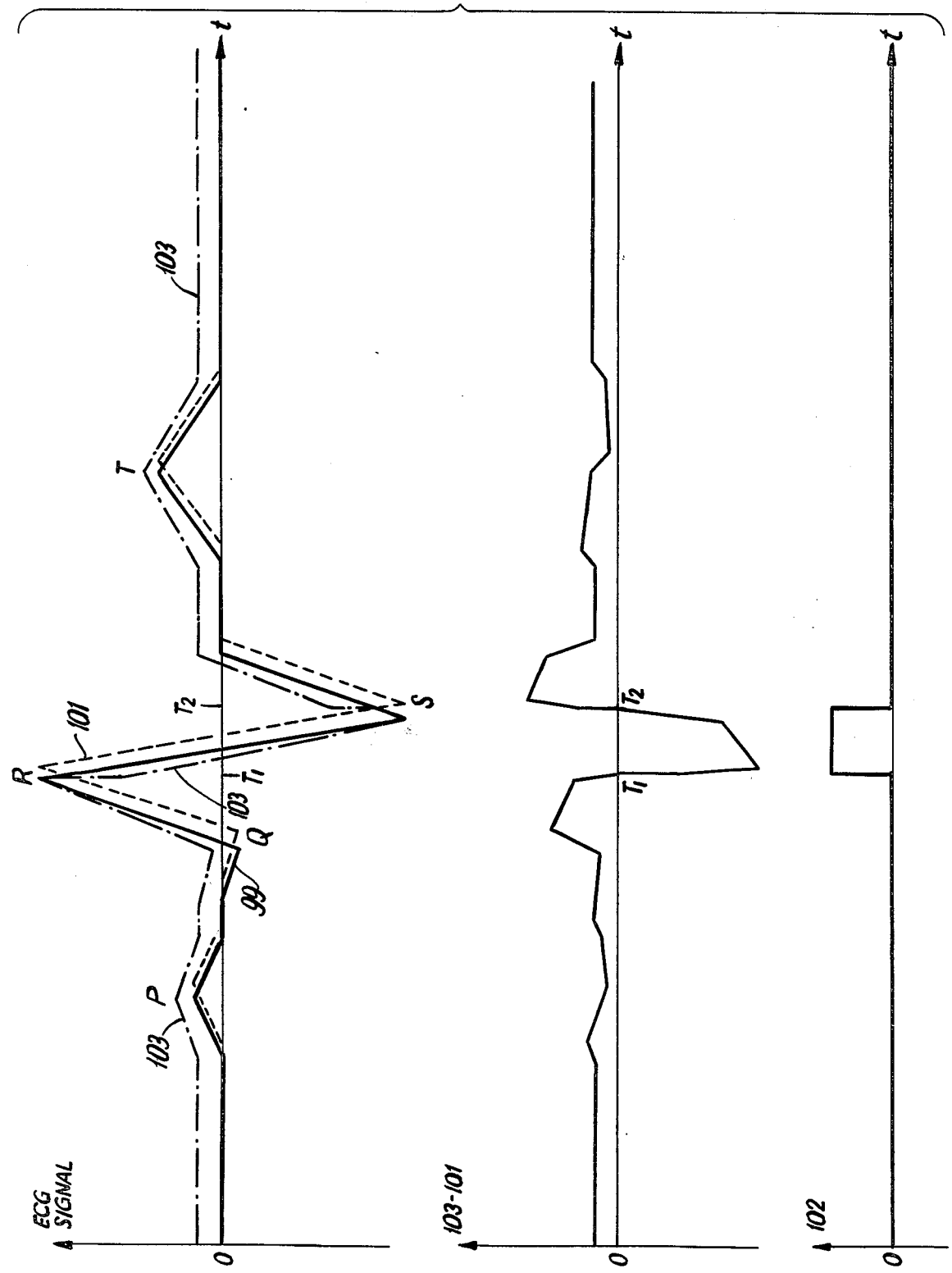

METHOD AND APPARATUS FOR LOCATING THE QRS PORTION OF AN ELECTROCARDIOGRAPHIC SIGNAL

BACKGROUND OF THE INVENTION

This invention relates to a method and improved apparatus for automatically locating the QRS portion of an electrocardiographic signal. More specifically, it relates to the use of an adaptive peak detector circuit which automatically locates the QRS portion of an applied electrocardiographic signal.

Typically, in the case of a normal heart, the amplitude of the QRS portion of the electrocardiographic signal predominates over the other portions, i.e., the P and T portions, of the electrocardiographic signal. Accordingly, many conventional methods of detecting the QRS portion of an electrocardiographic signal use some form of level comparator in conjunction with Schmitt trigger techniques to generate a synchronization (sync) signal whenever the amplitude of the applied electrocardiographic signal exceeds a predetermined level. However, these techniques are often not useful in the case of an abnormal heart where the QRS portion of the electrocardiographic signal is often obscured by the irregularities of the T portion of the electrocardiographic signal.

Furthermore, the conventional type of QRS detector is somewhat limited in its ability to automatically operate over the wide dynamic range of expected input electrocardiographic signals. Typically, the amplitude of the QRS portion of an electrocardiographic signal varies between 150 microvolts to 1.5 millivolts. Often, a manual adjustment is required to account for patient to patient variations in QRS signal strength.

Another limitation inherent in some of the conventional QRS detectors is the inability to operate with electrocardiographic signals in which the QRS portion is of negative polarity.

The above limitations and drawbacks associated with conventional types of QRS detectors are undesirable in certain applications. For example, it is often desired in certain medical equipment, in the presence of an input signal which varies in amplitude and polarity, to accurately establish a time reference and generate a sync pulse upon detection of the QRS portion of an electrocardiographic signal.

An example of such medical equipment is illustrated in copending application Ser. No. 854,537, filed Nov. 25, 1977, entitled, "Method and Apparatus for Characterizing Blood Flow through the Heart", assigned to the assignee of the present invention, and incorporated herein by reference. As described therein, a QRS detector is used to establish a time reference and generate a pulse used to synchronize a cathode ray tube display of the output of the left ventricle of the heart.

Accordingly, it is an object of the invention to provide a method for automatically locating the QRS portion of an electrocardiographic signal.

It is a further object of the invention to provide improved apparatus for automatically detecting the QRS portion of an electrocardiographic signal and generating a corresponding synchronization pulse.

It is still a further object of the invention to provide apparatus for automatically detecting the QRS portion of an electrocardiographic signal which varies in amplitude and polarity.

SUMMARY OF THE INVENTION

The foregoing and other objects and advantages which will be apparent in the following detailed description of the preferred embodiment, or in the practice of the invention, are achieved by the invention disclosed herein, which generally may be characterized as a method and improved apparatus for automatically locating the QRS portion of an electrocardiographic signal, the method comprising the steps of:

(a) adapting a terminal to receive an electrocardiographic signal;
(b) providing a time delayed replica of said electrocardiographic signal;
(c) biasing a first one of said electrocardiographic signal and said time delayed electrocardiographic signal; and
(d) comparing said biased electrocardiographic signal and the second one of said electrocardiographic signal and said time delayed electrocardiographic signal to provide a synchronization signal at the crossover point of said signals being compared;

and the apparatus comprising:

(a) means for adapting a terminal to receive an electrocardiographic signal;
(b) means for providing a time delayed replica of said electrocardiographic signal;
(c) means for biasing a first one of said electrocardiographic signal and said time delayed electrocardiographic signal; and
(d) means for comparing said biased electrocardiographic signal and the second one of said electrocardiographic signal and said time delayed electrocardiographic signal to provide a synchronization signal at the crossover point of said signals being compared.

BRIEF DESCRIPTION OF THE DRAWINGS

FIG. 5 is a timing diagram for the peak detector depicted in FIG. 4, showing triangular approximations to an electrocardiographic signal.

DETAILED DESCRIPTION OF PREFERRED EMBODIMENT

In order to afford a complete understanding of the invention and an appreciation of its advantages, a description of a preferred embodiment is presented below.

Figure 1:
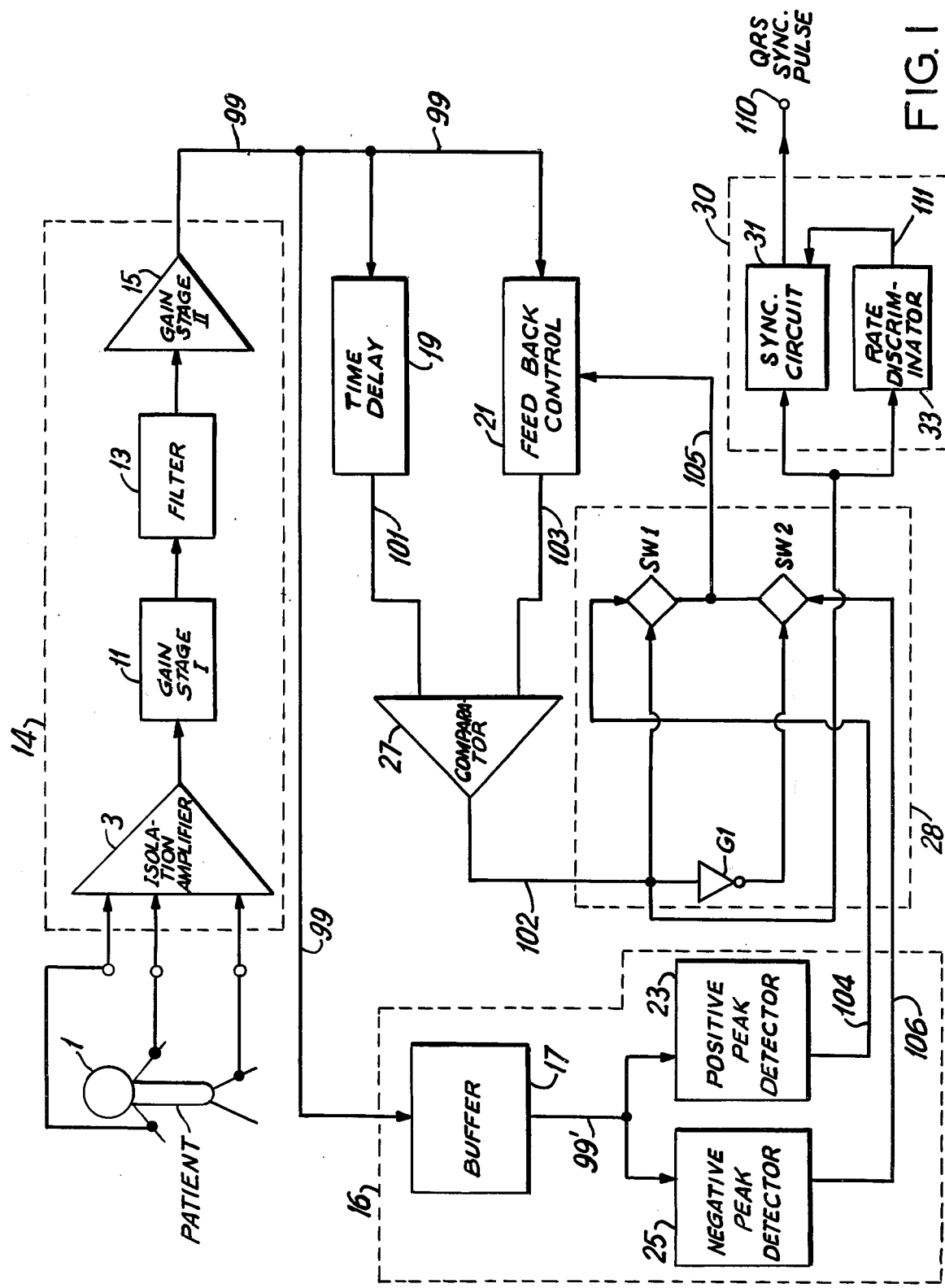
FIG. 1 is a block diagram of a preferred embodiment of the QRS detector, in accordance with the present invention.

Referring now to FIG. 1, a block diagram of a preferred embodiment of an adaptive QRS detector, in accordance with the present invention, is illustrated. As shown therein, the QRS detector consists of a number of functional networks comprising an analog signal processor 14, a peak detector 16, a time delay network 19, a feedback control network 21, a comparator network 27, a switching network 28 and a sync pulse network 30.

To better understand and appreciate the present invention, it may be helpful to understand in general, the waveform characteristics of a typical electrocardiographic signal.

Figure 2:
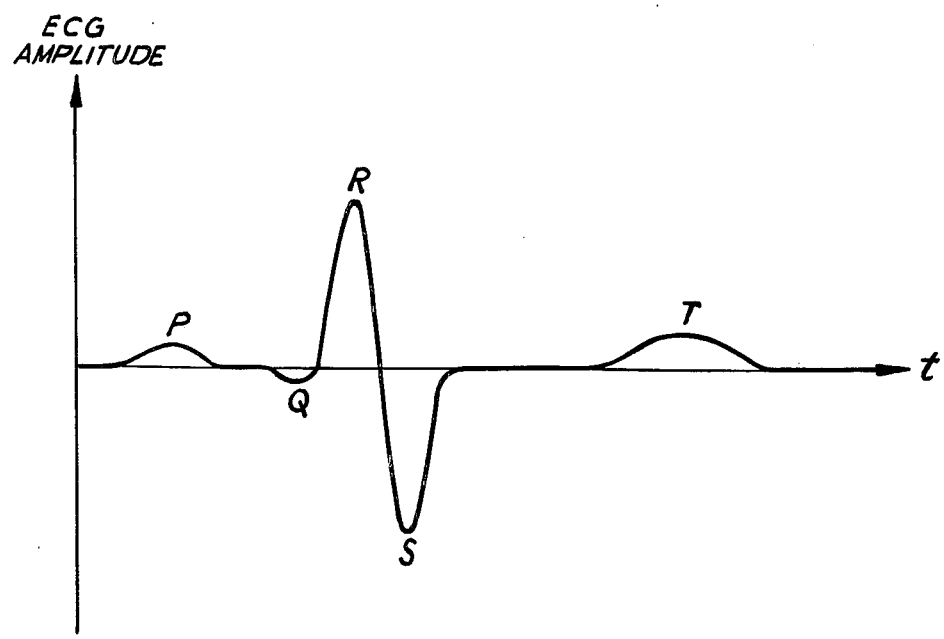
FIG. 2 illustrates a typical electrocardiographic signal waveform.

Referring now to FIG. 2, the waveform, corresponding to one complete cardiac cycle, of a typical electrocardiographic signal is illustrated. As shown therein, the electrocardiographic signal consists of a P portion, a QRS portion and a T portion. In the situation of a normal heart the amplitude of the QRS portion predominates over the amplitude of the P and T portions. However, in the situation of an abnormal heart any irregularities inherent in the T portion may obscure the QRS portion. Similarly, in the case of an abnormal heart the polarity of the QRS portion may be opposite that depicted in FIG. 2.

In the case of either a normal or abnormal heart, the QRS portion of the electrocardiographic signal exhibits an identifying property. In particular, the time rate of change of slope of the RS segment of the QRS portion of the electrocardiographic signal is substantially constant and the maximum of all waveform slopes. As will be more fully discussed below, this characteristic representative of the RS segment of the electrocardiographic signal is utilized to advantage in the QRS detector of the present invention.

Referring again to FIG. 1, a patient 1 is connected to a conventional isolation amplifier 3 by means of standard clinical electrocardiographic electrodes, right arm (RA), left arm (LA), and left leg (LL). Isolation amplifier 3 may consist, for example, of Analog Devices Model 276J. It is used to protect the patient against potential electrical hazards. The low level output signal 93 of isolation amplifier 3 is amplified to a suitable level by means of a first gain stage 11. The amplified output signal 95 is passed through a conventional filter 13. Filter 13 may consist, for example, of Data Delay Device Model 9158. Filter 13 removes unwanted higher frequency components, as well as 60 Hertz noise pickup and part of the low frequency muscle noise. The filtered output signal 97 is amplified to a usable level by means of a second gain stage 15. The first and second gain stages 11, 15 may be implemented using conventional amplifier networks.

The amplified output signal 99 of second gain 15 is applied to a conventional buffer stage 17. The output 99' of buffer stage 17 is connected to a positive peak detector 23 and a negative peak detector 25. Positive peak detector 23 and negative peak detector 25 may be implemented by means of conventional networks. The respective outputs of the positive peak detector 23 and the negative peak detector 25 are stored utilizing conventional techniques.

The amplified output signal 99 of the second gain stage 15 is also applied to a time delay network 19 and a feedback control network 21. Typically, the time delay network 19 consists of a conventional network configured to delay the input signal 99 a predetermined amount of time. The delay period is controlled by the values selected for the individual circuit elements comprising time delay network 19. Typically, the feedback control circuit 21 consists of a resistance summing network.

Figure 4:
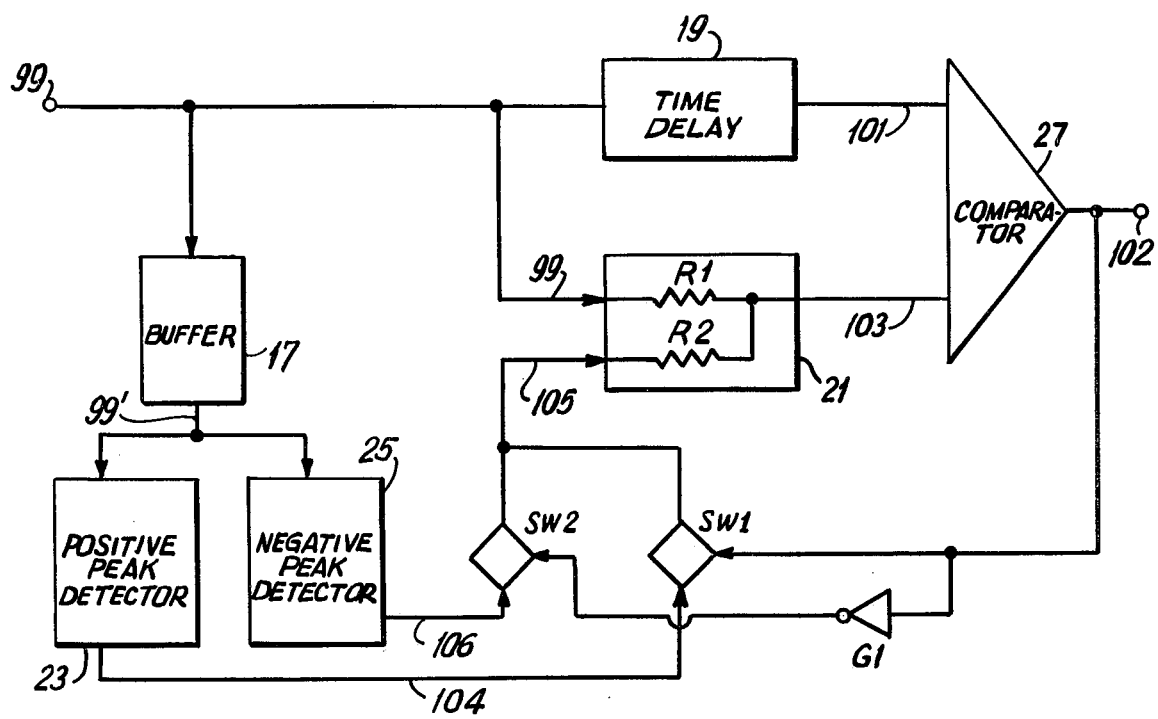
FIG. 4 is a block diagram of the peak detector utilized in the QRS detector, in accordance with the present invention.

The configuration of the feedback control circuit 21 is illustrated in greater detail in FIG. 4. As shown therein, the feedback control network 21 consists of summing resistors R1 and R2. The values of R1 and R2 are selected in accordance with the fractional amount of feedback signal 105 to be added to input signal 99 to produce a modified signal 103 having certain characteristics discussed more fully below. Depending upon whether the stored output of the positive peak detector 23 or the negative peak detector 25 is selected, the amplitude of feedback signal 105 may be either positive or negative.

To better understand and appreciate the present invention a basic understanding of the operation of the comparator portion of a slope detector may be helpful.

Figure 3A:
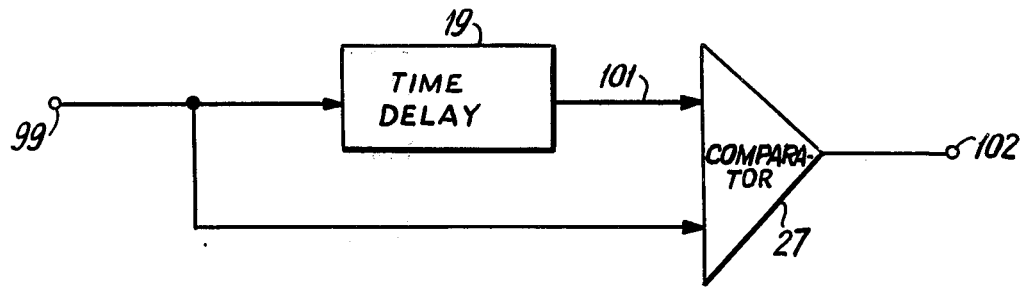
FIG. 3A is a block diagram of a portion of the comparator circuit utilized in the QRS detector of the present invention.
Figure 3B:
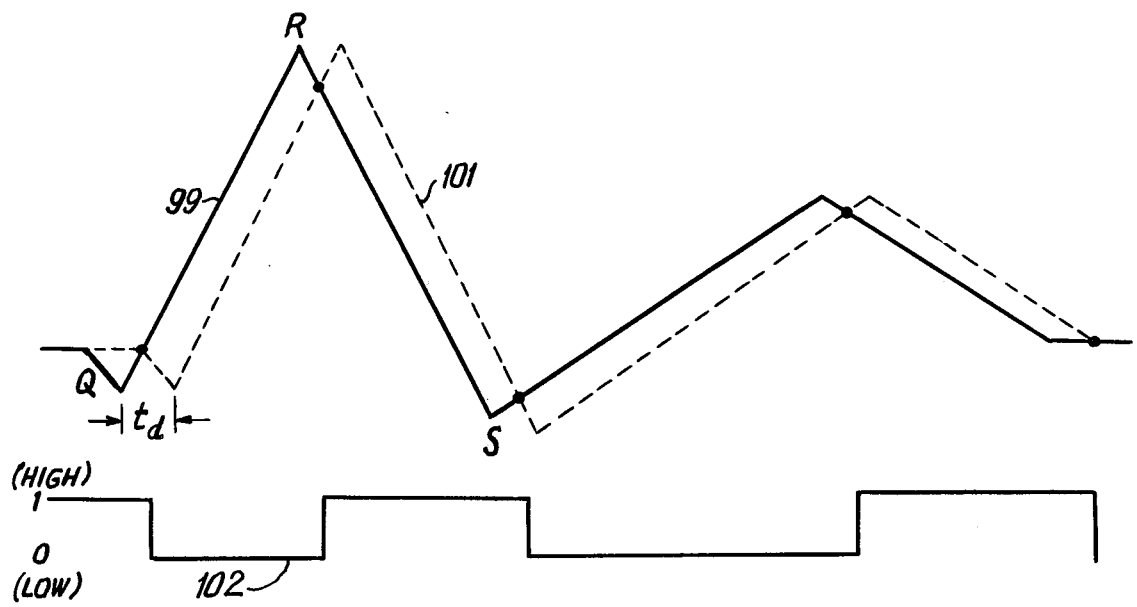
FIG. 3B illustrates the input and output waveforms of the portion of the comparator circuit illustrated in FIG. 3A.

Referring now to FIGS. 3A and 3B, the comparator portion of a slope detector utilizing time delay network 19 and the corresponding waveforms are illustrated. As shown therein, the input signal 99 is compared with a time delayed replica of itself 101. Each time the delayed signal 101 crosses the input signal 99 the output 102 of comparator 27 changes state, as illustrated in FIG. 3B. By properly selecting an appropriate value for $t_d$, the delayed signal 101 can be made to cross the RS segment of the QRS portion of input signal 99 at a desired point.

The low to high transition occurring at the output 102 of comparator 27 corresponding to the crossover point occurring during the RS segment of input signal 99 may be used to trigger an appropriate pulse forming network to provide an accurate indication of the detection of the QRS portion of the input electrocardiographic signal. In order to do this, however, the output 102 of comparator 27 must not experience any other low to high transitions during the same cardiac cycle.

In accordance with the present invention, a technique has been devised to modify input signal 99 to ensure that a comparison of the time delayed signal 101 with the modified signal 103 only results in one low to high transition at the output 102 of comparator 27 per cardiac cycle.

Referring now to FIG. 4, the network elements utilized to generate a modified signal 103 are illustrated. As shown therein, the modified signal 103 is generated by algebraically combining the input signal 99 with the feedback signal 105. The feedback signal 105 is the stored output of either the positive peak detector 23 or the negative peak detector 25. The selection of stored detector outputs 104 or 106 is controlled by the output 102 of comparator 27 in conjunction with switches SW1 and SW2 and inverter G1. Switches SW1 and SW2 may consist, for example, of Siliconix Model DG200.

The input signal 99 is applied to both the time delay network 19 and the feedback control network 21. The respective outputs 101 and 103 are compared in comparator 27. By properly selecting the amount and polarity of feedback signal 105 added to input signal 99 the modified signal output 103 of feedback control network 21 may be adjusted to ensure that the output 102 of comparator 27 changes state only once per cardiac cycle corresponding to the crossover occurring during the RS segment of the input electrocardiographic signal. To do this, the polarity of signal 105 is changed at the time of crossover causing a hysteresis effect which prevents further undesired comparator transitions.

Referring to the block diagram of FIG. 4 in conjunction with the waveforms depicted in FIG. 5, the fractional amount of feedback signal 105 to be added to input signal 99 to produce modified signal 103 is estimated as follows. To simplify the following analysis it is assumed that the network depicted in FIG. 4 has reached a steady state condition. Applying principles of superposition to the feedback control network 21 the following equation is readily obtained:

$$e_o = e_1 \times \frac{R_2}{R_1 + R_2} + e_2 \times \frac{R_2}{R_1 + R_2} \quad (2)$$

where
$e_1$=input signal 99
$e_2$=feedback signal 105
$e_o$=modified signal 103

For unvarying repetitive signals, the magnitudes and shapes of signals 99 and 105 would be well defined and the amount of hysteresis shown by signal 103 in FIG. 5 could be rigorously calculated using equation (2). However, actual electrocardiographic signals vary significantly from person to person, even in normal cases. Therefore, it is necessary to obtain certain information empirically. For example, it has been observed that a time delay of 10 milliseconds and a hysteresis of about 25% of the R or S peak will accommodate most normal and abnormal electrocardiographic signals and permit satisfactory detection of the RS slope. This amount of hysteresis will result if the coefficient of $e_1$ in equation (2) is 0.87 and the coefficient of $e_2$ is 0.13, as obtained from circuit measurements. The corresponding values of $R_1$ and $R_2$ may conveniently be, for example, 22K and 142K respectively.

Using equation (2) with the above coefficients, the signal relationships in FIG. 5 are constructed for a triangular approximation to the electrocardiographic waveform. Taking FIG. 5 in conjunction with the block diagram in FIG. 4, and assuming that steady state conditions have been reached, operation of the circuit is as follows.

Input signal 99 is applied to time delay circuit 99, buffer 17 and feedback control network 21. The output of time delay circuit 19 is signal 101 occurring later in time than signal 99. Buffer 17 drives positive peak detector 23 and negative peak detector 25 which have detected and stored the R and S peaks respectively of the buffered input signal 99'. The output 104 of positive peak detector 23 is controllably switched by output 102 of comparator 27 via switch SW1 and the output 106 of negative peak detector 25 is controllably switched by output 102 of comparator 27 via switch SW2 such that either SW1 or SW2 is always on but not both. The circuit of FIG. 4 is configured such that SW1 is generally on so that signal 105 at time t=0, for example, is the output 104 of positive peak detector 23.

Taking FIGS. 4 and 5 in conjunction with equation (2), the output 103 of feedback control circuit 21 at time t=0 is a fraction of the output 104 of positive peak detector 23 since signal 99 is zero at this time. During the P wave interval, a fraction of signal 99 is added to signal 105 according to equation (2) and signal 103 remains positive without intersecting any other waveform. Similarly, during the Q wave portion, signal 99 becomes negative but when added to signal 105, the resultant signal 103 remains positive. During the peak of the R wave, signals 103 and 99 coincide since signal 99 is near or equal to the stored positive peak value. From time t=0 to time t=$T_1$ the curve showing the differential input 103-101 to comparator 27 has remained positive. At time t=$T_1$ signal 103 becomes less positive than signal 101 since the fractional portion due to signal 99 has been reduced sufficiently in magnitude. At this time, output 102 of comparator 27 changes in polarity as shown in FIG. 5 causing SW1 to be disabled and enabling SW2. The transition causes output 106 of negative peak detector 25 to be applied to feedback control network 21 via SW2. The resulting negative polarity applied to feedback control network 21 causes signal 103 to drop instantaneously in magnitude by an amount governed by equation (2) demonstrating a hysteresis effect.

Comparator 27 holds its new polarity as signals 103 and 99 reach the S wave portion of the electrocardiographic signal. At time t=$T_2$ signal 103 becomes more positive than signal 101 so that the differential input 103-101 to comparator 27 is again positive and the output 102 of comparator 27 is restored to its previous state. SW2 is now disabled by signal 102 and inverter G1, and SW1 is enabled again, and the resulting change in polarity of signal 105 causes signal 103 to instantaneously increase in magnitude again demonstrating hysteresis. During the remainder of the cardiac cycle, the input to comparator 27 remains positive and the comparator output signal 102 undergoes no further transitions.

By having properly selected the values of R1 and R2 the amplitude of feedback signal 105 was adjusted to ensure that the amplitude of the modified signal 103 does not decrease below the amplitude of the delayed signal 101 for the duration of the cardiac cycle. This causes the differential input across comparator 27 to remain positive with respect to the zero reference level for the duration of the cardiac cycle. Since the output 102 of comparator 27 does not experience any more low to high transitions no additional sync pulses are generated during the cardiac cycle.

Referring again to FIG. 1, the output 102 of comparator 27 is used to trigger a conventional pulse shaping network comprising a sync circuit 31 and a rate discriminator circuit 33. Typically, the sync circuit 31 comprises a single shot multivibrator which is triggered on the low to high transition at the output 102 of comparator 27. To preclude false triggering the rate discriminator circuit 33, which typically comprises conventional gating means, is utilized to inhibit any spurious low to high transitions which may occur at the output 102 of comparator 27 during the duration of the cardiac cycle. To preclude losing any QRS sync pulses, the duration of the inhibit gate at the output 11 of the rate discriminator circuit 33 may be programmed to match the characteristics of the patient's cardiac cycle.

Figure 6:
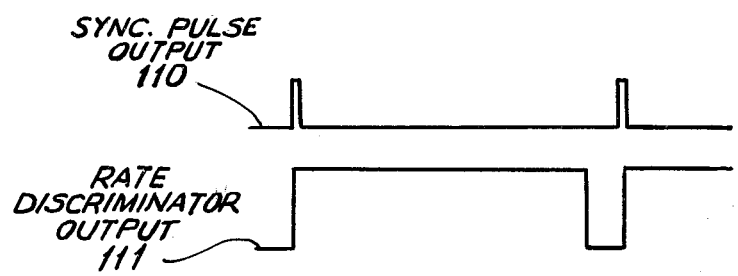
FIG. 6 illustrates the output waveforms of the pulse shaping network, in accordance with the present invention.

FIG. 6 illustrates typical waveforms generated at various points of the pulse shaping network. As shown therein, the rate discriminator output 111 is used to inhibit false triggering of the sync circuit 31 during the interval between detection of successive QRS portions of the input electrocardiographic signal.

Although the QRS portion of the input signal 99 was depicted as a positive triangular waveform, the same result would be obtained if the QRS portion of the input signal 99 was a negative triangular waveform. Only one sync pulse per cardiac cycle corresponding to the QRS portion of the input electrocardiographic signal is generated.

Similarly, the same result is obtained if the amplitude of either the P portion or the T portion of the waveform depicted in FIG. 5 exceeds the amplitude of the QRS portion. The operation of the circuit is independent of the relative amplitudes and polarities of the various portions of the electrocardiographic signal. It relies on the properties associated with the slope of the RS portion of the electrocardiographic signal. By controlling the time delay $t_d$ and the amplitude of the feedback signal 105 the circuit can detect any desired change in slope of any shape signal.

Although the circuit as described uses the low to high transition at the output 102 of comparator 27 to trigger a pulse forming network to generate a sync pulse output 110, the circuit could operate equally as well by utilizing the high to low transition at the output of the comparator to trigger the pulse forming network.

Similarly, alternate embodiments may include variations of the embodiment described above. For example, instead of modifying the input electrocardiographic signal by adding a positive bias voltage to it and comparing the resulting biased electrocardiographic signal with a time delayed replica of the input electrocardiographic signal, the same result is obtained if the input electrocardiographic signal is time delayed and biased negatively and then compared with the input electrocardiographic signal.

It is clear that the above description of the preferred embodiment in no way limits the scope of the present invention which is defined by the following claims.

What is claimed is:

1. A method for automatically detecting the QRS portion of an electrocardiographic signal comprising the steps of:
   (a) adapting a terminal to receive said electrocardiographic signal;
   (b) providing a time delayed replica of said electrocardiographic signal;
   (c) biasing a first one of said electrocardiographic signal and said time delayed electrocardiographic signal; and
   (d) comparing said biased electrocardiographic signal and the second one of said electrocardiographic signal and said time delayed electrocardiographic signal to provide a synchronization signal at the crossover point of said signals being compared.

2. The method of claim 1 further comprising the steps of:
   (a) providing a control signal having a magnitude that is a function of the amplitude of the peak of the QRS portion of said electrocardiographic signal;
   (b) updating said control signal to reflect the magnitude of the peak of the QRS portion immediately preceeding the QRS portion being time delayed; and
   (c) providing a bias signal responsive to said control signal having a magnitude and polarity that is a function, respectively, of the peak amplitude and polarity of the immediately preceeding QRS portion of said electrocardiographic signal.

3. The method of claim 2 further comprising the step of applying a positive bias to said electrocardiographic signal.

4. The method of claim 2 further comprising the step of applying a negative bias to said time delayed electrocardiographic signal.

5. Apparatus for automatically detecting the QRS portion of an electrocardiographic signal comprising:
   (a) means for adapting a terminal to receive said electrocardiographic signal;
   (b) means for providing a time delayed replica of said electrocardiographic signal;
   (c) means for biasing a first one of said electrocardiographic signal and said time delayed electrocardiographic signal; and
   (d) means for comparing said biased electrocardiographic signal and the second one of said electrocardiographic signal and said time delayed electrocardiographic signal to provide a synchronization signal at the crossover point of said signals being compared.

6. Apparatus as recited in claim 5 further comprising:
   (a) means for providing a control signal having a magnitude that is a function of the amplitude of the peak of the QRS portion of said electrocardiographic signal;
   (b) means for updating said control signal to reflect the magnitude of the peak of the QRS portion immediately preceeding the QRS portion being time delayed; and
   (c) means for providing a bias signal responsive to said control signal having a magnitude and polarity that is a function, respectively, of the peak amplitude and polarity of the immediately preceeding QRS portion of said electrocardiographic signal.

7. Apparatus as recited in claim 6 further comprising means for applying a positive bias to said electrocardiographic signal.

8. Apparatus as recited in claim 6 further comprising means for applying a negative bias to said time delayed electrocardiographic signal.

9. Apparatus for automatically detecting the QRS portion of an electrocardiographic signal comprising:
   (a) a terminal adapted to receive said electrocardiographic signal;
   (b) a time delay circuit coupled to said electrocardiographic signal to provide a delayed electrocardiographic signal;
   (c) bias means to bias a first one of said electrocardiographic signal and said time delayed electrocardiographic signal; and
   (d) a comparator circuit to compare said biased electrocardiographic signal and the second one of said electrocardiographic signal and said time delayed electrocardiographic signal to provide a synchronization signal at the crossover point of said signals being compared, said synchronization signal providing an indication of the location of the QRS portion of said electrocardiographic signal.

10. Apparatus for automatically detecting the QRS portion of an electrocardiographic signal comprising:
    (a) analog signal processing means responsive to said electrocardiographic signal;
    (b) peak detecting means responsive to the output of said analog signal processing means, said peak detecting means including positive peak detecting means and negative peak detecting means;
    (c) means for storing the respective outputs of said positive peak detecting means and said negative peak detecting means;
    (d) first signal processing means responsive to the output of said analog signal processing means;
    (e) second signal processing means responsive to the output of said analog signal processing means;
    (f) means for comparing the outputs of said first signal processing means and said second signal processing means;
    (g) means responsive to the output of said comparing means for controllably selecting the stored output of one of said positive peak detecting means and said negative peak detecting means;

(h) means for applying said selected output to said second signal processing means to be algebraically combined with the output of said analog signal processing means; and (i) means responsive to the output of said comparing means for generating a signal indicating detection of the QRS portion of said electrocardiographic signal.

11. Apparatus as recited in claim 10 wherein said analog signal processing means includes an isolation network, a filter network and at least one amplifier network.

12. Apparatus as recited in claim 11 wherein said peak detecting means includes a storage network.

13. Apparatus as recited in claim 12 wherein said first signal processing means includes a time delay network.

14. Apparatus as recited in claim 13 wherein said second signal processing means includes a resistance summing network.

15. Apparatus as recited in claim 14 wherein said comparing means includes a comparator circuit.

16. Apparatus as recited in claim 15 wherein said controllably selecting means includes at least one switch.

17. Apparatus as recited in claim 16 wherein said generating means includes a pulse shaping network.

18. Apparatus for automatically detecting the QRS portion of an electrocardiographic signal comprising:

(a) a multi-stage analog signal processing network adapted to receive said electrocardiographic signal;

(b) a peak detector network connected to the output of said analog signal processing network, said peak detector network including a positive peak detector and a negative peak detector;

(c) a memory for storing the respective outputs of said positive peak detector and said negative peak detector;

(d) a time delay network connected to the output of said analog signal processing network;

(e) a resistance summing network comprising a first resistor and a second resistor, said first resistor connected to the output of said analog signal processing network;

(f) a comparator network connected to the respective outputs of said time delay network and said resistance summing network;

(g) a switching network connected to the output of said comparator network for controllably selecting the stored output of one of said positive peak detector and said negative peak detector;

(h) means for applying said selected output to said second resistor to be algebraically combined with the output of said analog signal processing network; and (i) a pulse forming network connected to the output of said comparator network for generating a pulse whenever the output of said comparator network experiences a predetermined change of state.

19. Apparatus as recited in claim 18 wherein said analog signal processing network includes an isolation amplifier coupled to said electrocardiographic signal.

20. Apparatus as recited in claim 19 wherein said peak detector network further includes a buffer amplifier connected between the output of said analog signal processing network and each of said positive peak detector and said negative peak detector.

21. Apparatus as recited in claim 20 wherein said time delay network is configured to cause the output of said time delay network to cross the output of said resistance summing network at a point corresponding to the RS segment of said electrocardiographic signal.

22. Apparatus as recited in claim 21 wherein said switching network includes at least one switch.

23. Apparatus as recited in claim 22 wherein said pulse forming network generates a pulse whenever the output of said comparator network experiences a low to high transition.

24. Apparatus as recited in claim 22 wherein said pulse forming network generates a pulse whenever the output of said comparator network experiences a high to low transition.

25. Apparatus as recited in claim 20 wherein said time delay network is configured to cause the output of said time delay network to cross the output of said resistance summing network at a point following the RS segment of said electrocardiographic signal.

26. Apparatus as recited in claim 25 wherein said switching network includes at least one switch.

27. Apparatus as recited in claim 26 wherein said pulse forming network generates a pulse whenever the output of said comparator network experiences a high to low transition.

28. Apparatus as recited in claim 26 wherein said pulse forming network generates a pulse whenever the output of said comparator network experiences a low to high transition.

* * * * *

UNITED STATES PATENT AND TRADEMARK OFFICE
CERTIFICATE OF CORRECTION

PATENT NO. : 4,192,318
DATED : March 11, 1980
INVENTOR(S) : Dam, Naim G. et al

It is certified that error appears in the above-identified patent and that said Letters Patent are hereby corrected as shown below:

Column 3, Line 50, after "gain" add --stage--.

Column 5, Lines 6, 7, 8 and 9, fix equation to read:

$$e_o = e_1 \times \frac{R_2}{R_1+R_2} + e_2 \times \frac{R_1}{R_1+R_2}$$

Column 6, Line 49, change "11" to --111--.

Signed and Sealed this

Twenty-eighth Day of October 1980

[SEAL]

Attest:

SIDNEY A. DIAMOND

Attesting Officer

Commissioner of Patents and Trademarks